United States Patent [19]

Ueda

[11] 4,408,598
[45] Oct. 11, 1983

[54] ENDOSCOPE WITH AN AIR-LIQUID SUCTION DEVICE

[75] Inventor: Yasuhiro Ueda, Kokubunji, Japan

[73] Assignee: Olympus Optical Co., Ltd., Tokyo, Japan

[21] Appl. No.: 324,655

[22] Filed: Nov. 24, 1981

[30] Foreign Application Priority Data

Dec. 26, 1980 [JP] Japan ................................ 55/185941

[51] Int. Cl.³ .............................................. A61B 1/00
[52] U.S. Cl. ...................................................... 128/4
[58] Field of Search ......................................... 128/3–8, 128/276, 277, 278, 240

[56] References Cited

U.S. PATENT DOCUMENTS 4,193,406 3/1980 Jinotti ............................ 128/204.18
4,261,343 4/1981 Ouchi et al. ............................ 128/4
4,270,525 6/1981 Furihata ................................. 128/4

FOREIGN PATENT DOCUMENTS 53-36632 9/1978 Japan ..................................... 128/6

Primary Examiner—Kyle L. Howell
Assistant Examiner—Max F. Hindenburg

[57] ABSTRACT

An endoscope comprises an air-liquid selector valve and a suction control valve attached to a control section of the endoscope, a common tube extending through an insertion section, having one end connected with the suction control valve and the other end opened at the distal end portion of the insertion section of the endoscope, a connecting tube for connecting the suction control valve and the air-liquid selector valve. The air-liquid selector valve has a feed-air port, a feed-liquid port, and a piston-cylinder for selectively connecting the ports with the connecting tube, and the suction control valve has a suction port and a piston-cylinder for selectively connecting the suction port and the connecting tube with the common tube.

8 Claims, 5 Drawing Figures

ENDOSCOPE WITH AN AIR-LIQUID SUCTION DEVICE

BACKGROUND OF THE INVENTION

This invention relates to an endoscope with an air-liquid suction device.

Some endoscopes are provided with an air-liquid suction device for feeding air or liquid into the body cavity or removing mucus or the like from it by suction.

Conventionally, in the aforesaid air-liquid suction device, an air-liquid selector valve and a suction control valve are attached to a control section of an endoscope, and a feed-air tube, a feed-liquid tube, and a suction tube are passed through an insertion section connected with the control section so that the distal ends of these tubes open on the distal end face of the insertion section, and that the proximal ends of the tubes are connected with the two valves, severally. With the prior art suction device of this type, air and liquid are fed through the feed-air and -liquid tubes by selectively operating the air-liquid selector valve, and suction is performed by means of the suction tube by operating the suction control tube.

In such construction, however, the insertion section need be thick enough to contain the three tubes therein, and hence is too thick for a patient to overcome with ease the pain of insertion of the insertion section into his body. Accordingly, there is a great demand for a reduction in diameter of the insertion section, especially in endoscopes, such as bronchoscopes, whose insertion section are to be inserted in very narrow lumina and may cause quite severe pain to patients.

SUMMARY OF THE INVENTION

The object of this invention is to provide an endoscope having a common single tube in its insertion section adapted for all of air feed, liquid feed, and suction, thus reducing the diameter of the insertion section.

BRIEF DESCRIPTION OF THE DRAWINGS

FIGS. 1 to 5 show an endoscope according to an embodiment of this invention, in which FIG. 1 is a general perspective view, FIG. 2 is a schematic view of a control section, and FIGS. 3 to 5 are sectional views of an air-liquid suction device illustrative of different operating states.

DETAILED DESCRIPTION OF THE PREFERRED EMBODIMENT

Figure 1:
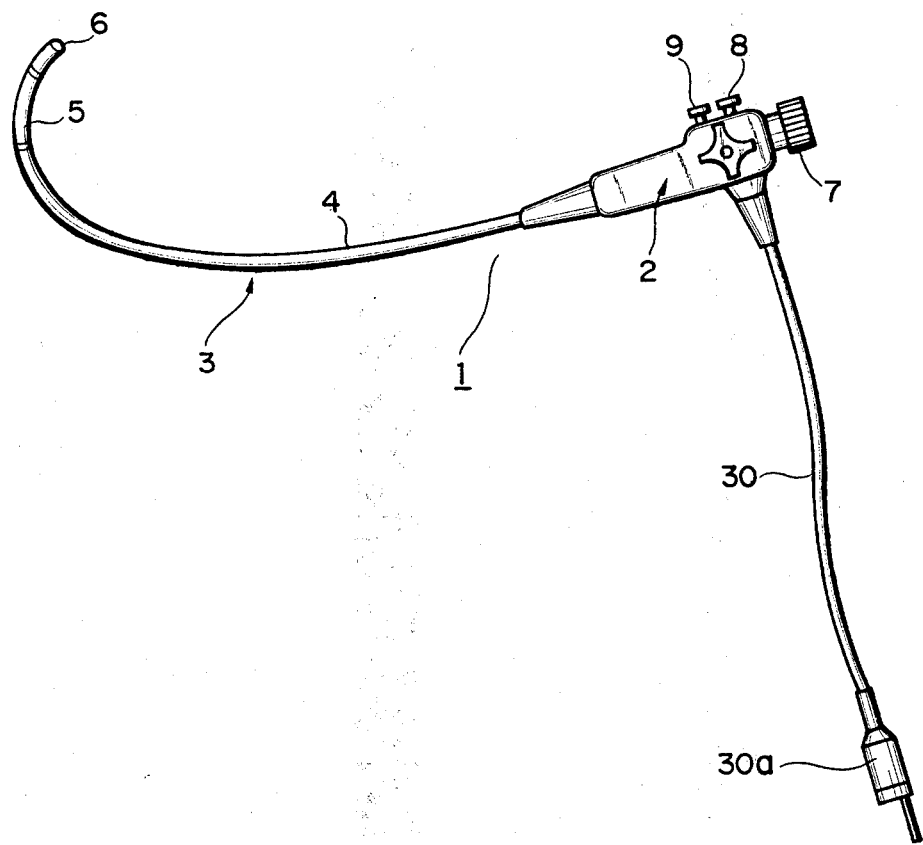
Figure 2:
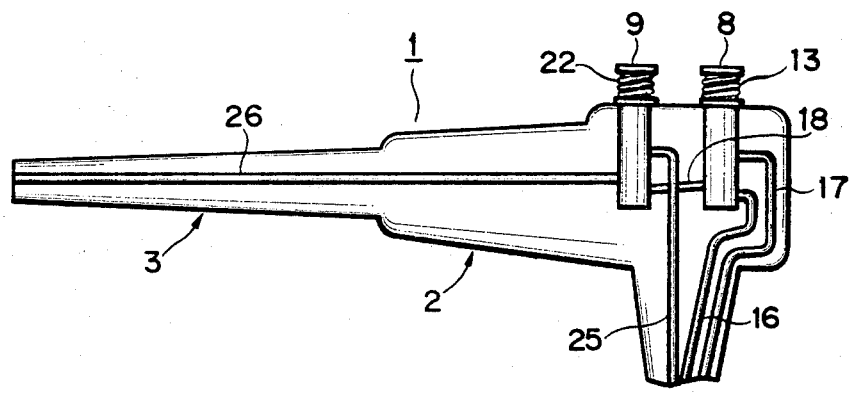

Now there will be described an embodiment of this invention with reference to the accompanying drawings. In FIG. 1, numeral 1 denotes an endoscope which comprises a control section 2 capable of external operation, and an elongate insertion section 3 whose proximal end is connected with the control section 2 to be inserted in the body of a patient. The insertion section 3 is composed of a flexible portion 4, a bent portion 5, and a distal end portion 6 connected in succession from the side of the control section 2. The bent portion 5 may be bent to a desired degree by operating a control knob (not shown) attached to the control section 2. The control section 2 is connected with a light guide cable 30 having a connector 30a at one end portion to be coupled to a light supply unit (not shown), and includes an eyepiece portion 7, an air-liquid selector valve 8, and a suction control valve 9.

Figure 3:
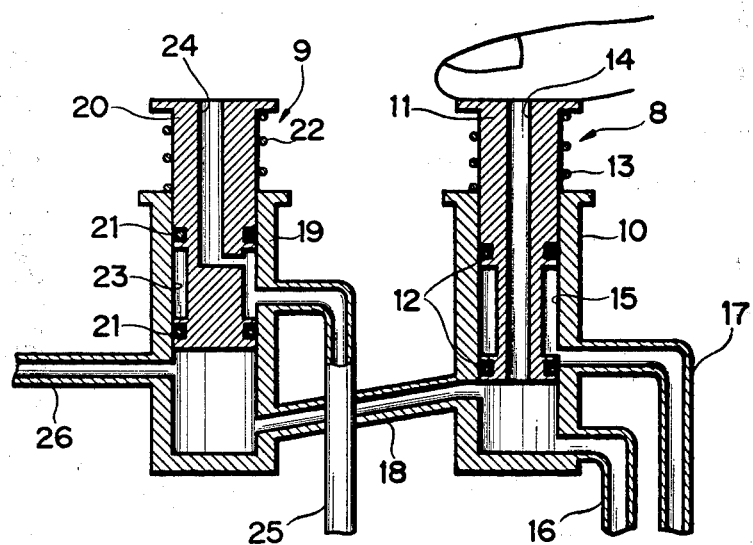

The air-liquid selector valve 8 and the suction control valve 9 are constructed as shown in FIGS. 2 to 5. The air-liquid selector valve 8 includes a first cylinder 10 which, fixed to the control section 2, is opened at the top and closed at the bottom. A first piston 11 with O-rings 12 thereon is fitted closely in the first cylinder 10 so as to be able to reciprocate therein, and is urged in a direction to project from the cylinder 10 by a first compression coil spring 13 which is disposed between the top flange of the piston 11 and the top end face of the cylinder 10. The first piston 11 has an air discharge hole 14 extending along the axial direction of the piston 11 and opening at both top and bottom of the piston 11, and a first annular communication groove 15 formed in the outer peripheral surface of the end portion of the piston 11 located inside the first cylinder 10. Formed in the peripheral wall of the first cylinder 10 are a feed-air port connected with one end of a feed-air tube 16, a feed-liquid port located above the feed-air port and connected with one end of a feed-liquid tube 17, and a port located between the feed-air and -liquid ports and connected with one end of a connecting tube 18. In the air-liquid selector valve 8, as shown in FIG. 3, the piston 11 is normally urged to its uppermost position by the first spring 13 to block up the feed-liquid tube 17, allowing the feed-air tube 16 to communicate with the open air by means of the cylinder 10 and the air discharge hole 14.

The suction control valve 9 includes a second cylinder 19 which is fixed to the control section 2 in parallel with the first cylinder 10 and is opened at the top and closed at the bottom. A second piston 20 with O-rings 21 thereon is fitted closely in the second cylinder 19 so as to be able to reciprocate therein, and is urged in a direction to project from the cylinder 19 by a second compression coil spring 22 which is disposed between the top flange of the piston 20 and the top end face of the cylinder 19. Bored in the second piston 20 is an air inlet hole 24 which opens at one end on the top end face of the piston 20 and at the other end into a second annular communication groove 23 formed in the outer peripheral surface of the end portion of the piston 20 located inside the cylinder 19. Formed in the peripheral wall of the second cylinder 19 are a port connected with the other end of the connecting tube 18, a suction port located above the connecting tube 18 and connected with one end of a suction tube 25, and a port located between these two ports and connected with one end of a common tube 26. In the suction control valve 9, as shown in FIG. 3, the piston 20 is normally urged to its uppermost position by the second spring 22 to allow the suction tube 25 to communicate with the open air by means of the second communication groove 23.

The feed-air tube 16, the feed-liquid tube 17, and the suction tube 25 extend from the control section 2 to pass through the light guide cable 30 so that the other ends of these tubes are connected with feed-air, feed-liquid, and suction devices (not shown), respectively, by means of the connector 30a. The common tube 26 extends from the control section 2 to open on the distal end face of the insertion section 3.

Now there will be described the operation of the endoscope with the above-mentioned construction. First, when the feed-air, feed-liquid, and suction devices are operated with the air-liquid selector valve 8 and the suction control valve 9 off, air fed into the feed-air tube 16 passes through the first cylinder 10 to be discharged from the air discharge hole 14 into the open air, while liquid fed into the feed-liquid tube 17 is prevented by the first piston 11 from flowing into the first cylinder 10. Further, a sucking force is produced inside the suction tube 25, whereby the open air is sucked into the suction tube 25 through the air inlet hole 24 and the second communication groove 23.

Figure 4:
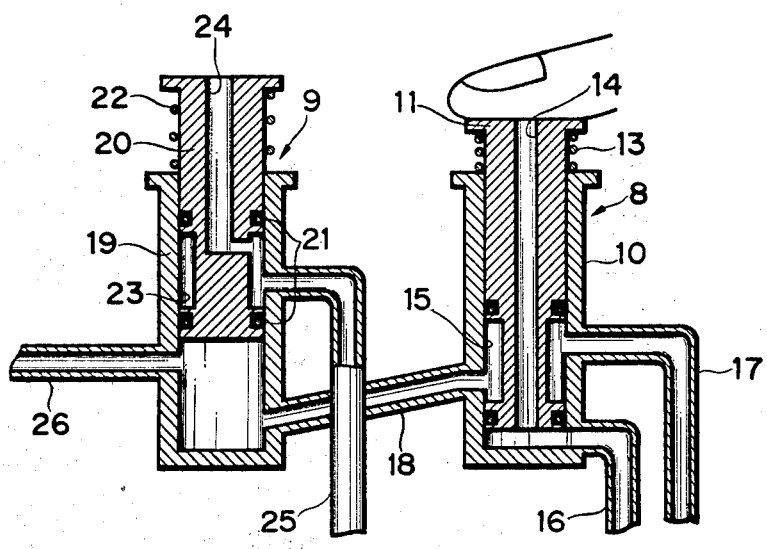
Figure 5:
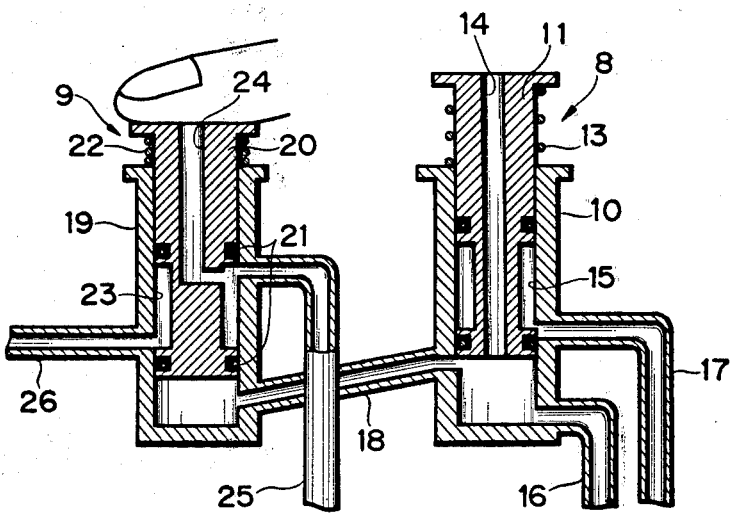

In air-feed operation, the air discharge hole 14 of the first piston 11 is blocked up with an operator's finger, as shown in FIG. 3. Then, the air having so far been being discharged from the air discharge hole 14 into the open air comes to flow through the connecting tube 18 into the second cylinder 19, and passes therefrom through the common tube 26 to flow out into the body cavity from the distal end of the insertion section 3 which is inserted in the body cavity. In liquid-feed operation, on the other hand, the first piston 11 is depressed against the restoring force of the first spring 13, as shown in FIG. 4. Then, the feed-liquid tube 17 is caused to communicate with the connecting tube 18 by means of the first communication groove 15, so that the liquid having so far been prevented from flowing by the first piston 11 is allowed to flow through the first communication groove 15 and the connecting tube 18 into the second cylinder 19, and passes therefrom through the common tube 26 to flow out into the body cavity. In sucking out mucus or the like from the body cavity, moreover, the suction tube 25 is caused to communicate with the common tube 26 by means of the second communication groove 23 by depressing the second piston 20 against the restoring force of the second spring 22 while blocking up the air inlet hole 24 of the second piston 20 with the finger. Then, the sucking force of the suction tube 25 having so far been sucking in the open air acts on the interior of the body cavity through the common tube 26, so that mucus or the like in the body cavity is sucked into the suction tube 25 via the common tube 26 and the second communication groove 23.

In the endoscope with the above-mentioned construction, the air-liquid selector valve and the suction control valve are connected with a single common tube so that air feed, liquid feed, and suction may selectively be performed by means of the common tube. It is therefore possible to reduce the diameter of the insertion section through which the common tube extends.

In the above-mentioned embodiment, the air-liquid selector valve and the suction control valve are connected by means of a connecting tube. Such a connecting tube, however, is unnecessary if these two valves are formed directly in contact or in one united body.

What is claimed is:

1. An endoscope comprising:
   an insertion section including a proximal end and a distal end portion;
   a control section connected with the proximal end of said insertion section;
   an air-liquid selector valve and a suction control valve attached to said control section;
   a common tube extending through said insertion section, having one end connected with said suction control valve and the other end opened at the distal end portion of said insertion section; and
   connecting means for connecting said suction control valve and said air-liquid selector valve,
   said air-liquid selector valve having a feed-air port, a feed-liquid port, and selector means for selectively connecting said ports with said connecting means, and
   said suction control valve having a suction port and selector means for selectively connecting said suction port and said connecting means with said common tube.

2. An endoscope according to claim 1, wherein said air-liquid selector valve includes a first cylinder fixed to said control section and having said feed-air and -liquid ports formed therein, and a first piston slidably inserted in said first cylinder and constituting said selector means, said suction control valve includes a second cylinder fixed to said control section and having said suction port formed therein, and a second piston slidably inserted in said second cylinder and constituting said selector means, said common tube being connected at one end thereof with said second cylinder, and said connecting means includes a connecting tube with one and the other end connected with said first and second cylinders, respectively.

3. An endoscope according to claim 2, wherein said first cylinder is a cylinder with one end opened and the other end closed, said feed-air port being located nearer to said other end of said first cylinder than said one end of said connecting tube is, and said feed-liquid port being located nearer to said one end of said first cylinder than said one end of said connecting tube is, and said first piston can slide between an air feed position where said connecting tube is connected with said feed-air port and a liquid feed position where said connecting tube is connected with said feed-liquid port.

4. An endoscope according to claim 3, wherein said first piston has an air discharge hole connecting the interior of said first cylinder with the open air, and a first communication groove connecting said feed-air port and said connecting tube.

5. An endoscope according to claim 4, wherein said air-liquid selector valve includes urging means for keeping said first piston in said air feed position.

6. An endoscope according to claim 2, wherein said second cylinder is a cylinder with one end opened and the other end closed, said other end of said connecting tube being located nearer to said other end of said second cylinder than said one end of said common tube is, and said suction port being located nearer to said one end of said second cylinder than said one end of said common tube is, and said second piston can slide between an air or liquid feed position where said common tube is connected with said connecting tube and a suction position where said common tube is connected with said suction port.

7. An endoscope according to claim 6, wherein said second piston has an air inlet hole connecting said suction port with the open air, and a second communication groove connecting said suction port and said common tube.

8. An endoscope according to claim 7, wherein said suction control valve includes urging means for keeping said second piston in said air or liquid feed position.

* * * * *